United States Patent [19]

Suschitzky et al.

[11] 4,038,413
[45] July 26, 1977

[54] TREATING IRON DEFICIENCY ANAEMIA

[75] Inventors: John Louis Suschitzky; David Rutherford, both of Loughborough, England

[73] Assignee: Fisons Limited, London, England

[21] Appl. No.: 664,280

[22] Filed: Mar. 5, 1976

Related U.S. Application Data

[62] Division of Ser. No. 522,591, Nov. 11, 1974, Pat. No. 3,960,911.

[30] Foreign Application Priority Data

Nov. 21, 1973 United Kingdom ............... 54002/73
July 17, 1974 United Kingdom ............... 31609/74

[51] Int. Cl.² .......................................... A61K 31/295
[52] U.S. Cl. .................................................. 424/295
[58] Field of Search ........................................ 424/295

Primary Examiner—Stanley J. Friedman
Attorney, Agent, or Firm—Merriam, Marshall, Shapiro & Klose

[57] ABSTRACT

There are described compounds of formula I,

I

-continued

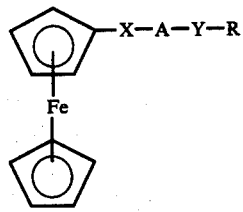

in which R is allyl, chlorine, bromine, phenyl, or phenyl substituted by one or more halogen or alkyl groups, one of X and Y is a group —CO—, —CHOH— or —CH$_2$— and the other is an exocyclic carbon-carbon bond linking the ferrocenyl or the R group respectively to the —A— group, A contains 5, 6 or 7 carbon atoms and is an ethylenically unsaturated (the double bond being connected to the carbon atom which is connected to X), unsubstituted (except by X and Y) cyclic hydrocarbon group; or is a saturated cyclic hydrocarbon group substituted by X and Y and, when X is a group —CO—, optionally substituted on the carbon atom to which Y is attached by an —OH group, and X and Y are attached to adjacent carbon atoms on the A group. There are also described processes for the production of compounds of formula I and haematinic compositions containing them.

6 Claims, No Drawings

TREATING IRON DEFICIENCY ANAEMIA

This is a division of application Ser. No. 522,591, filed Nov. 11, 1974, now U.S. 3,960,911.

This invention relates to new compounds, a method for their preparation and compositions containing them.

According to our invention we provide compounds of formula I,

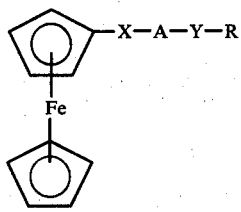

I in which
R is alkyl, chlorine, bromine, phenyl, or phenyl substituted by one or more halogen or alkyl groups,
one of X and Y is a group —CO—, —CHOH— or —CH$_2$— and the other is an enocyclic carbon-carbon bond linking the ferrocenyl or the R group respectively to the —A— group,
A contains 5, 6 or 7 carbon atoms and is an ethylenically unsaturated (the double bond being connected to the carbon atom which is connected to X), unsubstituted (except by X and Y), cyclic hydrocarbon group; or is a saturated cyclic hydrocarbon group substituted by X and Y and, when X is a group —CO—, optionally substituted on the carbon atoms to which Y is attached by an —OH group, and
X and Y are attached to adjacent carbon atoms on the A group.

According to our invention we also provide a process for the production of a compound of formula I, which comprises
a. producing a compound of formula Ia,

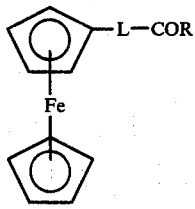

Ia in which
R is as defined above, and
L is an unsubstituted cycloalkene group containing 5, 6 or 7 carbon atoms (the double bond being connected to the carbon atom which is directly connected to the ferrocenyl radical), by (i) reacting ferrocene with a compound of formula II, Rx(CH$_2$)$_n$COR    II in which
R is as defined above,
n is 4, 5 or 6, and
Rx is —CN, —COOH or an acid halide or anhydride thereof, or (ii) cyclizing and dehydrating a compound of formula III,

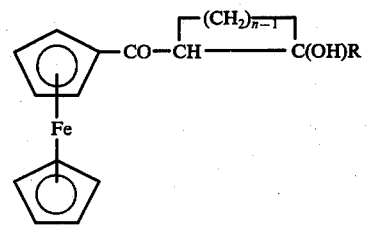

III in which
n and R are as defined above,
b. producing a compound of formula Ib, ![Ib structure with —CO—CH—[(CH$_2$)$_{n-1}$]—C(OH)R]

Ib in which R and n are as defined above, by cyclizing a compound of formula III,
c. producing a compound of formula Ic, ![Ic structure with —Xa—A—Ya—R]

Ic in which
R and A are as defined above, and
one of Xa and Ya is a group —CHOH— or —CH$_2$— and the other is a carbon-carbon bond linking the ferrocenyl or the R group to the A group, Xa and Ya being attached to adjacent carbon atoms in the A group,
by selective reduction of a compound of formula Ia, Ib or If respectively,
d. producing a compound of formula Id, ![Id structure with —Xb—A—Yb—R]

Id in which
A and R are as defined above, and
one of Xb and Yb is a —CO— group and the other is a carbon-carbon bond linking the ferrocenyl or the R group to the A group, Xb and Yb being attached to adjacent atoms in the A group,
by selective oxidation of a compound of formula Ic in which one of Xa and Ya is a —CHOH— group, e. producing a compound of formula Ia in which R is phenyl or phenyl substituted by one or more halogen or alkyl groups, by reacting a compound of formula V,

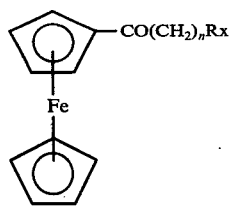

V in which n and Rx are as defined above, with benzene or benzene substituted by up to five halogen or alkyl groups, or f. producing a compound of formula If,

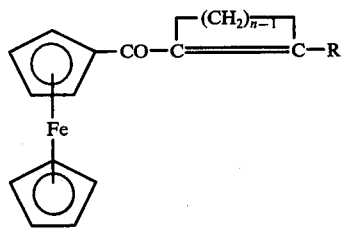

If in which

R and n are as defined above, by dehydrating a compound of formula Ib.

The reaction of processes (a)(i) and (e) may be carried out in a solvent which is inert under the reaction conditions, for example methylene chloride. The reaction is preferably carried out under Friedel-Crafts reaction conditions, for example in the presence of a Lewis acid such as aluminium chloride. The reaction is preferably carried out at a temperature of from about 0° to 100° C and preferably from 0° to 45° C. The anhydride may be a symmetrical anhydride or may be a mixed anhydride. Examples of suitable acids from which the mixed anhydride may be derived are acetic, benzylic and trifluoroacetic acid. When the group Rx is a —CN the product will be an imine which will be hydrolyzed to the desired compound. We prefer the group Rx to be an acid halide group. Process (a)(i) is preferably not used to produce compounds in which R is chlorine or bromine.

The cyclization and dehydration of process (a)(ii) may be carried out by subjecting the compound of formula III to acidic conditions, e.g. a mixture of sulphuric and acetic acids, or to a Lewis acid in a solvent which is inert under the reaction conditions, e.g., methylene chloride. The reaction may be carried out at a temperature of from about 0° to about 100° C, e.g. at about 20° C.

The cyclization of process (b) is preferably carried out under basic conditions and in a suitable, preferably polar, solvent, e.g. dioxane or ethanol. The base may conveniently be an alkali metal base, e.g. a sodium base. Specifically the process may be carried out using sodium hydride in dioxane or sodium hydroxide in ethanol. The process may conveniently be carried out at a temperature of from about 0° to 100° C, and for a time of from about 30 minutes to 24 hours depending on the temperature used.

The reduction of process (c) may be carried out catalytically, e.g. using palladium on charcoal. The reduction may conveniently be carried out at a temperature of from 20° to 80° C, e.g. about room temperature (20° C). The reduction may be carried out at atmospheric pressure, but is preferably carried out at greater than atmospheric pressure. Alternatively the reduction may be carried out chemically using reagents and reaction conditions known to effect the reduction of —CO— to —CHOH— or —CH$_2$—; or of —CHOH— to —CH$_2$—. Suitable reducing agents include NaAlH$_2$(OCH$_2$CH$_2$OCH$_3$)$_2$. The chemical reduction may conveniently be carried out at a temperature of from about 0° to 50° C in a solvent which is inert under the reaction conditions, e.g. methylene chloride or ethanol. When reduction to a —CH$_2$— group is desired a Clemmensen reduction may be used.

The selective oxidation of process (d) may be carried out in a solvent which is inert under the reaction conditions, e.g. methylene chloride. A suitable oxidizing agent is chromium trioxide dipyridine complex. The reaction may conveniently be carried out at a temperature of from 0° to 50° C, and preferably at about room temperature (20° C).

Process (f) may be carried out under substantially the same conditions as process (b), but production of the compound of formula I (b) is favoured by lower reaction temperatures, e.g. below about 20° C, and shorter reaction times.

Compounds of formula II are either known or may be made from known compounds using conventional techniques known per se.

The compounds of formula III may be made by carrying out process (a)(i) at a temperature of between about 0° and −25° C. During the production of the compound of formula III some of the final product of formula Ia may be formed directly. We have found that, in general, use of a lower temperature and shorter reaction time tends to favour the formation of the compound of formula III as opposed to the compound of formula Ia. Compounds of formula III in which R is phenyl or phenyl substituted by up to five halogen or alkyl groups may also be made by reacting a compound of formula V with benzene or benzene substituted by up to five halogen or alkyl groups. The reaction may be carried out under conditions similar to those set out above for process (a)(i). Compounds of formula V may be made from known compounds using conventional techniques known per se.

The compounds of formula III have the same utility as the compounds of formula I, but we have found that the compounds of formula I possess considerable advantages over those of formula III.

It will be observed that process (a)(ii) may be an intermediate step in process (a)(i) and that process (b) may be an intermediate step in process (f).

Furthermore both process (b) and process (a)(ii) involve cyclization of a compound of formula III. In processes (a)(i), (a)(ii) and (b) a mixture of compounds of formulae Ia, Ib, III and it may be produced and the desired compound separated from the mixture using conventional techniques, e.g. crystallization from suitable solvents such as ethyl acetate; or chromatography on an inert medium such as silica gel using organic eluents, such as toluene or petroleum ether/ethyl acetate mixtures. The separation of any such mixtures and the choice of optimum reaction conditions and reagents to produce the greatest yield of any particular product is well within the ordinary skill of those working in this field.

The compounds of formula I are useful because they possess pharmacological activity in animals. In particular, the compounds are useful as haematinics (as is shown by the rapid correction of iron deficiency anaemia, as determined by following haemoglobin regeneration, in anaemic rats to which the compounds have been administered orally: Lawrence and Bacharach, Evaluation of Drug Activities - Pharmacometrics, Academic Press, New York 1964 page 563) and are useful in the treatment of iron deficiency in man and other animals, e.g. pigs, horses and cattle. The compounds are particularly useful for the treatment of iron deficiency anaemia in women. A substantial proportion of the dose administered to rats is transformed into physiologically acceptable iron stores (ferritin) and is retained in organs such as the liver. The degree of storage may be determined by measuring the non-haem iron in the liver by the method of Torrance and Bothwell - South African Journal of Medical Science 1962 Volume 32 page 9. The compounds are particularly indicated for oral administration.

For the above mentioned use, the dosage administered will, of course, vary depending upon the compound employed, mode of administration and treatment desired. However, in general, satisfactory results are obtained when administered orally at a daily dosage of from about 1 milligram to 250 milligrams active ingredient per kilogram of animal body weight, preferably given 1 to 3 times a day, or in sustained release form. For man the total dosage is in the range of from about 50 milligrams to about 2,000 milligrams active ingredient, and unit dosage forms suitable for oral or parenteral administration comprise from about 20 to about 2,000 milligrams of the active ingredient.

The compounds according to the invention may be formulated into pharmaceutical compositions with pharmaceutically acceptable adjuvants, carriers or diluents. The nature of the adjuvant, carrier or diluent will depend in part on the intended mode of administration of the composition. Examples of suitable adjuvants, carriers and diluents are: for tablets and dragees - lactose, starch, talc, stearic acid or an effervescent couple; for capsules - tartaric acid or lactose; for orally administered solutions or suspensions and for injectable solutions - water, alcohols, glycerin or vegetable oils; and for suppositories - natural or hardened oils or waxes. The compounds may also be formulated as a paste, granule, chewable gum or tablet, jelly, drinkable ampule, and/or in combination with a human or animal feedstuff, e.g. bread. In addition, the compositions may also include other pharmacologically active components such as Vitamin B12, folic acid, Vitamin C (and/or other vitamins), an analgesic, e.g. aspirin, an anthelmintic or an oral contraceptive. The composition may also contain suitable preserving, stabilizing and wetting agents, solubilizers and sweetening and colouring agents and flavourings. If desired, the composition may be formulated in sustained release form or in enteric coated form. Compositions for oral administration are preferred. We prefer to use the compound of formula I in a solid particulate form having a mass median diameter of less than 10 and preferably less than 5 microns.

The compounds of this invention possess pharmacological properties of an order not demonstrated by similar known compounds.

When R is an alkyl group we prefer it to contain from 1 to 6 carbon atoms, e.g. methyl, ethyl or butyl. When R is phenyl substituted by halogen or alkyl we prefer mono substitution in the position para or ortho to Y. When R is phenyl substituted by halogen we prefer the halogen to be chlorine or fluorine. When R is phenyl substituted by alkyl we prefer the alkyl to contain 1 to 10, and more preferably 1 to 6 carbon atoms. We also prefer the A group to contain 6, or more preferably 5, carbon atoms. Where the group A is ethylenically unsaturated we prefer the double bond to link the two carbon atoms to which X and Y are attached. We also prefer the group Y to be a —CO— group. Thus as a particularly preferred group we provide compounds of formula Ia in which R is a benzene ring, the benzene ring optionally being substituted by a single chlorine atom, or by a single methyl group, and L is a cyclopentene ring in which the double bond links the carbon atom attached to the —CO— group and the carbon atom attached to the ferrocene nucleus.

Certain of the compounds of formula I exist in optically active form, and we therefore provide the optical isomers themselves and mixtures, including racemic mixtures, thereof. The compounds may be resolved into their optical isomers using conventional techniques.

The invention is illustrated, but in no way limited by the following Examples in which the temperatures are in degrees centigrade.

EXAMPLE 1

1-Benzoyl-2-ferrocenylcyclopentene a. 6-Oxo-6-phenylhexanoyl chloride

6-Oxo-6-phenylhexanoic acid (10.3g; 50 mmole), thionyl chloride (25 ml) and dry benzene (150 ml) were heated under reflux for 3 hours. The reagent and solvent were removed on the rotary evaporator. A further 100 ml of benzene was added and the solution again evaporated under reduced pressure (to remove last traces of thionyl chloride). The quantitatively formed, analytically pure brown solid (mp 53°-6°) was used directly in the Friedel-Crafts acylation of step (b).

b. 1-Benzoyl-2-ferrocenylcyclopentene

6-Oxo-6-phenylhexanoyl chloride (9.0g; 0.04 mole) and ferrocene (7.44g; 0.04 mole) in methylene chloride (150 ml) were stirred at 0° and aluminium chloride (5.34g; 0.04 mole) was added over 40 minutes at 0°. The mixture was stirred at 0° (2 hr), and then at room temperature (90 min). More aluminium chloride (4g; 0.03 mole) was added and the reaction mixture was heated under reflux for 90 minutes. Water was added, the organic layer run off, and the aqueous layer extracted with methylene chloride (100 ml). The combined organic layers were washed with water (3 × 200 ml), and dried (sodium sulphate) to yield a brown oil. The portion of this oil which was insoluble in hot cyclohexane was discarded and the remainder (2.7g) was subjected to preparative thin layer chromatography to yield 2.1g (15%) of pure 1-benzoyl-2-ferrocenylcyclopentene as a brown solid mp 136°-7°.

The procedure described in the preceding paragraph may be replaced by the following procedure:

Ferrocene (186g; 1 mole) and 6-oxo-6-phenylhexanol chloride (224.5g; 1 mole) were dissolved in 1,2- dichloroethane (2 l), and aluminium chloride (133.3g; 1 mole) was added with stirring at room temperature over 2 hr. The mixture was left stirring for a further 0.5 hr and then poured into water (4 l) and the oily solution extracted thoroughly with chloroform (4x). The extracts were washed with water (3x), saturated sodium bicarbonate (2x) and water, dried ($Na_2SO_4$), concentrated to about 500 ml and stirred with alumina (400g) for 3 hr. The alumina was removed by filtration and the filtrate yielded a deep red oil which crystallized from petroleum ether (bp 60°-80°; 800 ml) + chloroform (100 ml). Two further crops were obtained on concentrating the mother liquor. Total yield 155g. Chromatography of the mother liquors on silica was performed. Toluene eluted ferrocene (11g) and toluene/3% ethyl acetate eluted a further pure sample of required compound (39.7g).

The total yield of pure 1-benzoyl-2-ferrocenylcyclopentene was 195g (55%) mp 136°-7°.

EXAMPLE 2

1-Ferrocenoyl-2-phenylcyclopentene

6-Phenyl-6-oxohexanoylferrocene (5.61g; 15 mmole) in sodium dried dioxane (150 ml) was heated under reflux with sodium hydride (0.72g; 30 m mole) for 3 hr. The mixture was cooled and treated carefully with water (200 ml) when a brown solid precipitated, which was filtered off to yield 4.3g (76%) of nearly pure 1-ferrocenoyl-2-phenylcyclopentene. An analytical sample (3.7g; 69%) was obtained by one recrystallization from cyclohexane. mp 163°-4°.

EXAMPLE 3

1-Benzyl-2-ferrocenylcyclopentane and 1-(α-Hydroxybenzyl)-2-ferrocenylcyclopentane 1-Benzoyl-2-ferrocenylcyclopentene (7.12g; 0.02 mole) in ethanol (150 ml) was submitted to hydrogenation in the presence of palladium on charcoal (0.8g) at 25 lb/sq inch above atmospheric pressure. After 2 days at room temperature, the mixture was filtered (to remove the Pd/C) and the ethanol removed to yield a brown oil, which was chromatographed on silica gel. Toluene eluted pure 1-benzyl-2-ferrocenylcyclopentane (3.5g), mp ca 30°. 'HNMR $\delta$, 7.13 (m 5H); 4.07 (m 9H), 2.5 - 1.0 (multiplets 10H)$\gamma$ max 2950, 1205, 815, 700, and toluene/3% ethylacetate eluted pure 1-(α-Hydroxybenzyl)-2-ferrocenylcyclopentane; a semi solid at room temperature. 'HNMR $\delta$ 7.18 (S, 5H); 4.1 (S, 5H); 4.33 → 4.05 (multiplets; 1H+4H); 3.2 (doublet of doublets; 1H) 2.35 - 1.2 (m, 8H)$\gamma$ max 3300 $cm^{-1}$.

EXAMPLE 4

1-Benzoyl-2-ferrocenyl-cyclopentane 1-(α-Hydroxybenzyl)-2-ferrocenyl cyclopentane (360 mg; 1 mmole) was added to a suspension of chromium trioxide dipyridine complex (1.6g; sixfold excess) in calcium chloride dried methylene chloride (25 ml) at room temperature with stirring for 1 hr. The suspension was filtered, the organic solution was washed with 2N NaOH (2 × 100 ml), 2N HCl (2 × 100 ml) and water (2 × 100 ml), and dried ($Na_2SO_4$) to yield a pale brown oil which crystallized on trituration with petroleum ether. Recrystallization from petroleum ether (bp 40°-60°) gave the desired product as a yellow solid (80 mg; 22%) mp 109°-110° IR:$\gamma$ max 1670 $cm^{-1}$ 'HNMR:$\delta$ 7.7 and 7.4 (multiplets 5H); 4.0 (s, 5H); 4.1 - 3.9 (m; 4H); 3.5 (m, 1H); 2.0 (m; 7H)

EXAMPLE 5

1-Ferrocenyl-2-(4-chlorobenzoyl)cyclopent-1-ene 5-(4-Chlorobenzoyl)pentanoic acid (9.6g; 0.04 mole) in toluene (50 ml) was heated under reflux for 4 hr with thionyl chloride (10 ml; excess). The toluene and excess thionyl chloride were evaporated under vacuum to yield the acid chloride as a pale brown solid which was used directly in the synthesis of the ferrocene derivative.

5-(4-Chlorobenzoyl)pentanoyl chloride (5.2g; 0.02 mole) in methylene chloride (100 ml) and ferrocene (3.75g; 0.02 mole) were stirred at 0.5° and aluminium chloride (2.7g; 0.02 mole) was added slowly over 0.5 hr. The mixture was stirred at 0.5° for 1.5 hr then water was added. The organic layer was separated. The aqueous layer was extracted with methylene chloride and the combined organic fractions were washed with water, dried (magnesium sulphate) and evaporated to yield a brown solid. This was recrystallized from petroleum ether (60°-80°) to yield pure 5-(4-chlorobenzoyl)pentanoyl ferrocene; 3.23g (40%); mp 103°-6°.

5-(4-Chlorobenzoyl)pentanoyl ferrocene (8.2g; 0.02 mole) and 5% (v/v) concentrated sulphuric acid in glacial acetic acid (200 ml) were stirred at room temperature for 1 hour, the mixture was poured into water and extracted with chloroform (3 × 100 mls.). The combined extracts were washed with saturated aqueous sodium bicarbonate, and water, dried (magnesium sulphate) and evaporated under vacuum to yield a red-brown oil which crystallized from pentane at 0°-5°. The solid was filtered off to yield pure 1-ferrocenyl-2-(4-chlorobenzoyl)cyclopent-1-ene; 2.5g (35%) mp 121°-3°.

EXAMPLE 6

1-Ferrocenyl-2-(3-methylbenzoyl)cyclopent-1-ene

The title compound was prepared by a similar sequence of reactions to those described in Example 5 using 5-(3-methylbenzoyl)pentanoylferrocene as starting material.

Yield: 8% mp 110°-3° C.

EXAMPLE 7

3-Benzoyl-2-ferrocenylcyclohexene

7-Oxo-7-phenylheptanoylferrocene (1.94g; 5 mmole) was dissolved in 5% $H_2SO_4$/acetic acid (40 ml; excess) at room temperature. The solution was stirred overnight and then poured into water (400 ml) and extracted with chloroform (3 × 200 ml). The organic layers were extracted with water, saturated aqueous sodium bicarbonate, and water, and dried ($Na_2SO_4$) to yield a brown oil. The crude product product was suspended in hot petroleum ether (bp 40°-60° C) and filtered. The filtrate was submitted to preparative thin layer chromatography on silica. The rain yellow band was eluted with petroleum ether/ethyl acetate 10:1) and gave 670 mg (36.2%) of pure 3-benzoyl-2-ferrocenylcyclohexene mp 127°-9° C.

EXAMPLE 8

1-Ferrocenoyl-2-hydroxy-2-phenylcyclohexane

6-Benzoylhexanoylferrocene [2.91g; 7.5 mmole] was dissolved in a solution of sodium hydroxide [0.3g; 7.5 mmole] in ethanol [100 ml] and stirred at room temperature for 16 hours.

Filtration and recrystallization from cyclohexanone gave the desired product [1.3g; 47%] mp 172°-3° C.

EXAMPLE 9

1-Chloro-2-ferrocenoylcyclopent-1-ene

Ferrocenoyl valeric acid (3g; 0.01 mole) in toluene (20 ml) was stirred for 4 hr at 0°-5° with oxalyl chloride (3.8 g; 0.03 mole). The toluene and excess oxalyl chloride were evaporated off under vacuum to yield a pale brown oil which was used directly.

This brown oil (ferrocenoyl valeroyl chloride) assumed to be 0.01 mole from the above preparation in methylene chloride (100 ml) was stirred at 0°-5° and aluminium chloride (1.3g; 0.01 mole) was added. Ice was then added and the organic layer was separated. The aqueous layer was extracted with chloroform. The combined organic fractions were washed with water, dried (magnesium sulphate) and evaporate to yield a red oil which was purified by dry-column chromatography on silica, which had been deactivated to Grade III by the addition of water, using 1:10 ethylacetate: petroleum ether as eluent, to yield pure 1-chloro-2-ferrocenoylcyclopent-1-ene, 150 mg; mp 102°.

EXAMPLE 10

1-Ferrocenyl-2-(2-fluorobenzoyl)cyclopent-1-ene 5-(2-Fluorobenzoyl)-pentanoylferrocene (16g, 0.04 mole) and 5% v/v concentrated sulphuric acid in glacial acetic acid (300 ml) were stirred for 15 minutes at room temperature and were then poured into water. The aqueous layer was extracted with chloroform. The combined extracts were washed with water, dried (magnesium sulphate) and evaporated under vacuum. The resulting oil was purified by preparative thin layer chromatography using silica gel, with toluene as eluent, to yield pure b 1-ferrocenyl-2-[2-fluorobenzoyl)cyclopent-1-ene as red crystals; 1.2g (8%) mp 90°-92°.

EXAMPLE 11

1-Benzoyl-2-ferrocenylcyclopentene

Ferrocenoylvaleric acid (3.13g; 0.01 mole) in methylene chloride (20 ml) was stirred at 0°-5° for 30 minutes while oxalyl chloride (5 ml) was added. After further stirring at room temperature for 30 minutes both the methylene chloride and excess oxalyl chloride were removed by evaporation at reduced pressure. The resulting light brown oil was used directly.

Ferrocenoylvaleryl chloride (prepared as above and assumed to be 0.01 mole) was diluted with methylene chloride (10 mls.) and benzene (20 mls.) and the solution was cooled to 0°-5°. Aluminum chloride (2.6g; 0.02 mole) was then added with stirring over 30 minutes. After further stirring at room temperature for 2 hours, ice was added to the reaction mixture. The organic layer was then separated and washed successively with water, aqueous sodium bicarbonate solution, and water, before being dried over sodium sulphate. Evaporation under reduced pressure produced a brown oil from which chromatography on silica gel with toluene/ethyl acetate provided a pure sample of the required compound (0.32g; 9% yield) mp 135°-7°.

We claim:

1. A pharmaceutical composition suitable for use in treating iron deficiency anaemia comprising, in a unit dose of from 20 to 2000 mg., a compound of formulas

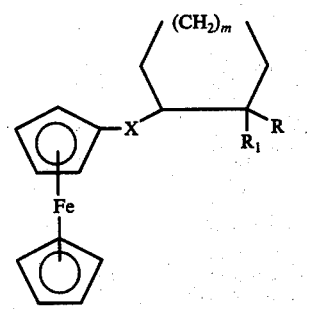

(1)

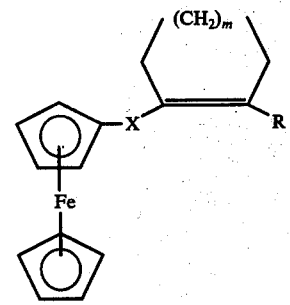

(2)

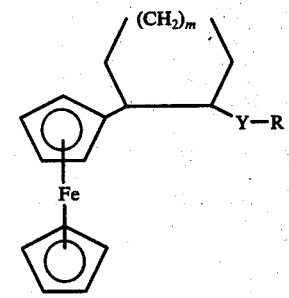

(3)

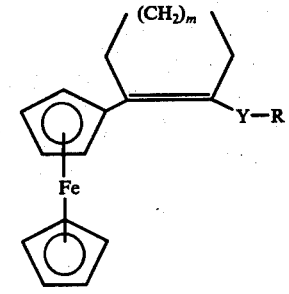

(4)

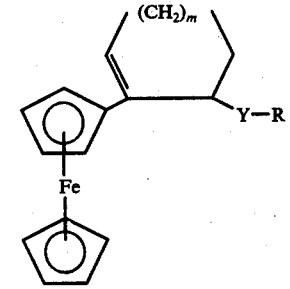

(5)

(6)

-continued

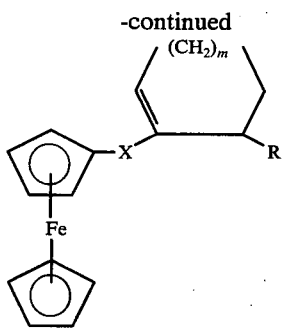

in which
R is alkyl, chlorine, bormine, phenyl, or phenyl substituted by one or more halogen or alkyl groups,
X is a group —CO—, —CHOH or —CH$_2$—,
Y is a group —CO—, —CHOH or —CH$_2$—,
m is an integer from 1 to 3, and
R$_1$ is hydrogen, or is hydrogen or —OH when X is —CO— as an active ingredient, in combination with a pharmaceutically acceptable adjuvant, diluent or carrier.

2. A composition according to claim 1 wherein said compound is
 1-ferrocenoyl-2-phenylcyclopentene,
 1-benzyl-2-ferrocenylcyclopentane,
 1-(α-hydroxybenzyl)-2-ferrocenylcyclopentane,
 1-benzoyl-2-ferrocenyl-cyclopentane,
 1-ferrocenyl-2-(4-chlorobenzoyl)cyclopent-1-ene,
 1-ferrocenyl-2-(3-methylbenzoyl)cyclopent-1-ene,
 3-benzoyl-2-ferrocenylcyclohexene,
 1-ferrocenoyl-2-hydroxy-2-phenylcyclohexane,
 1-chloro-2-ferrocenoylcyclopent-1-ene, or
 1-ferrocenyl-2-(2-fluorobenzoyl)cyclopent-1-ene.

3. A composition according to claim 1 wherein said compound is 1-benzoyl-2-ferrocenylcyclopentene.

4. A method for treating iron deficiency anaemia in animals, said method comprising administering to an animal having iron deficiency anaemia a therapeutically effective amount of a compound of the formulas

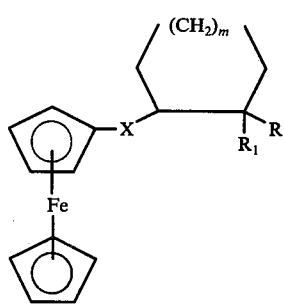

(1)

(2)

(3)

-continued

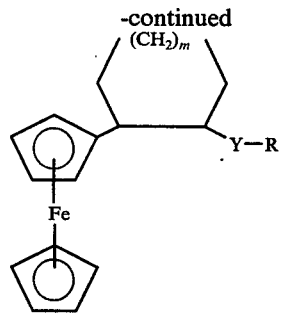

(4)

(5)

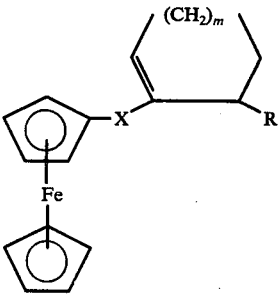

(6)

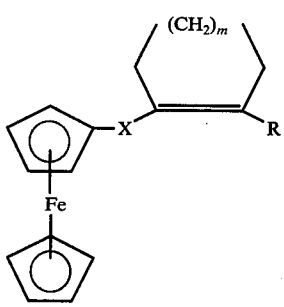

in which
R is alkyl, chlorine, bormine, phenyl, or phenyl substituted by one or more halogen or alkyl groups.
X is a group —CO—, —CHOH or —CH$_2$—,
Y is a group —CO—, —CHOH or —CH$_2$—,
m is an integer from 1 to 3, and
R$_1$ is hydrogen, or is hydrogen or —OH when X is —CO—.

5. A method according to claim 4 wherein said compound is
 1-ferrocenoyl-2-phenylcyclopentene,
 1-benzyl-2-ferrocenylcyclopentane,
 1-(α-hydroxybenzyl)-2-ferrocenylcyclopentane,
 1-benzoyl-2-ferrocenyl-cyclopentane,
 1-ferrocenyl-2-(4-chlorobenzoyl)cyclopent-1-ene,
 1-ferrocenyl-2-(3-methylbenzoyl)cyclopent-1-ene,
 3-benzoyl-2-ferrocenylcyclohexene,
 1-ferrocenoyl-2-hydroxy-2-phenylcyclohexane,
 1-chloro-2-ferrocenoylcyclopent-1-ene, or
 1-ferrocenyl-2-(2-fluorobenzoyl)cyclopent-1-ene.

6. A method according to claim 4 wherein said compound is 1-benzoyl-2-ferrocenylcyclopentene.

* * * * *

UNITED STATES PATENT AND TRADEMARK OFFICE
CERTIFICATE OF CORRECTION

PATENT NO. : 4,038,413
DATED : July 26, 1977
INVENTOR(S) : JOHN LOUIS SUSCHITZKY and DAVID RUTHERFORD It is certified that error appears in the above-identified patent and that said Letters Patent are hereby corrected as shown below:

In the first line of the Abstract which follows the structural formula, "allyl" should be --alkyl--.

Column 1, line 25, "enocyclic" should be --exocyclic--.

Column 1, line 34, "atoms" should be --atom--.

Column 4, line 62, "it" should be --If--.

Column 5, line 35, "total dosage" should read --total daily dosage--.

Column 5, line 68, "10 and" should be --10, and--.

Column 6, line 44, "(mp 53°-6°)" should be --(mp 53-56°)--.

Column 6, line 64, "136°-7°" should be --136-137°--.

Column 6, line 67, "phenylhexanol" should be --phenylhexanoyl--

Column 7, line 20, "136°-7°" should be --136-137°--.

Column 7, line 32, "163°-4°" should be --163-164°--.

Column 7, line 37, "ferrocencylcyclopentene" should be --ferrocenylcyclopentane--.

Column 8, line 25, "103°-6°" should be --103-106°--.

Column 8, line 37, "121°-3°" should be --121-123°--.

Column 8, line 46, "110°-3°" should be --110-113°--.

UNITED STATES PATENT AND TRADEMARK OFFICE
CERTIFICATE OF CORRECTION

PATENT NO. : 4,038,413
DATED : July 26, 1977
INVENTOR(S) : JOHN LOUIS SUSCHITZKY and DAVID RUTHERFORD It is certified that error appears in the above-identified patent and that said Letters Patent are hereby corrected as shown below:

Column 8, line 57, delete "product" second occurrence.

Column 8, line 60, "rain" should be --main--.

Column 8, line 61, "acetate 10:1)" should be --acetate (10:1)--.

Column 8, line 63, "127°-9°" should be --127-129°--.

Column 9, line 4, "172°-3°" should be --172-173°--.

Column 9, line 21, "evaporate" should be --evaporated--.

Column 9, line 67, "135°-7°" should be --135-137°--.

Column 12, line 51, after "groups", change the period (.) to a comma (,).

Signed and Sealed this

Twenty-ninth Day of November 1977

[SEAL]

Attest:

RUTH C. MASON
Attesting Officer

LUTRELLE F. PARKER
Acting Commissioner of Patents and Trademarks